(12) United States Patent
Henke et al.

(10) Patent No.: US 11,490,982 B2
(45) Date of Patent: Nov. 8, 2022

(54) MODULARLY STRUCTURED LID FOR A STERILE CONTAINER AND FILTER COVERING FOR SUCH A LID

(71) Applicant: AESCULAP AG, Tuttlingen (DE)

(72) Inventors: Matthias Henke, Fridingen (DE); Andreas Elisch, Rottweil (DE); Matthias Schweizer, Tuttlingen (DE); Stefan Thomas, Tuttlingen (DE); John Gray-Dreizler, Niedereschach (DE); Philipp Bohnenstengel, Steißlingen (DE); Thomas Sterk, Singen (DE); Betina Bernauer, Geisingen (DE)

(73) Assignee: Aesculap AG, Tuttlingen (DE)

( * ) Notice: Subject to any disclaimer, the term of this patent is extended or adjusted under 35 U.S.C. 154(b) by 293 days.

(21) Appl. No.: 16/636,107

(22) PCT Filed: Jul. 31, 2018

(86) PCT No.: PCT/EP2018/070732
§ 371 (c)(1),
(2) Date: Feb. 3, 2020

(87) PCT Pub. No.: WO2019/025441
PCT Pub. Date: Feb. 7, 2019

(65) Prior Publication Data
US 2020/0383745 A1  Dec. 10, 2020

(30) Foreign Application Priority Data

Aug. 3, 2017  (DE) .................... 10 2017 117 624.1

(51) Int. Cl.
*A61L 2/26* (2006.01)
*A61B 50/30* (2016.01)
*A61B 50/00* (2016.01)

(52) U.S. Cl.
CPC ............. *A61B 50/30* (2016.02); *A61L 2/26* (2013.01); *A61B 2050/007* (2016.02); *A61L 2202/182* (2013.01); *A61L 2202/24* (2013.01)

(58) Field of Classification Search
CPC .. A61L 2/26; A61L 2202/182; A61L 2202/24; A61B 50/30; A61B 50/31; A61B 50/33; A61B 2050/007
(Continued)

(56) References Cited

U.S. PATENT DOCUMENTS 4,915,913 A * 4/1990 Williams ............... B65D 45/24
436/1
5,080,874 A * 1/1992 Nichols ..................... A61L 2/26
206/508

(Continued)

FOREIGN PATENT DOCUMENTS

DE       10156937 A1    6/2003
DE    102004020803 A1   11/2005

(Continued)

OTHER PUBLICATIONS

International Search Report and Written Opinion for International Application No. PCT/EP2018/070732, dated Nov. 12, 2018, 8 pages.

(Continued)

*Primary Examiner* — Luan K Bui
(74) *Attorney, Agent, or Firm* — Christopher A. Rothe; Culhane Meadows, PLLC

(57) ABSTRACT

A modularly structured lid for a sterile container includes a lid component, which has at least one gas exchange portion, on which, on the inner side of a lid, at least one filter device can be arranged, and at least one filter covering by which the at least one gas exchange portion can be completely covered on an outside of the lid. The lid component has at least one (Continued)

standardized clip receiving portion and the filter covering has at least one standardized clip portion, by which the filter covering and the lid component can be interlockingly fixed to each other, and can be mounted and removed without tools. A sterile container can include such a lid and a filter covering for such a lid.

7 Claims, 2 Drawing Sheets

(58) Field of Classification Search
USPC ........... 206/363, 370, 438; 220/254.2, 254.7, 220/361, 366.1, 367.1, 370, 371; 422/297, 300
See application file for complete search history.

(56) References Cited

U.S. PATENT DOCUMENTS

| | | | | |
|---|---|---|---|---|
| 5,524,755 A * | 6/1996 | Deeds | ............... | A61L 2/06 206/439 |
| 6,585,942 B1 * | 7/2003 | Bussell | ............... | A61B 50/31 206/349 |
| 6,715,628 B1 * | 4/2004 | Nichols | ............... | A61L 2/26 220/361 |
| 7,381,385 B2 * | 6/2008 | Gleichauf | ............... | A61L 2/26 422/297 |
| 9,005,541 B2 * | 4/2015 | Kreidler | ............... | A61L 2/26 422/292 |
| 2004/0256269 A1 | 12/2004 | Gleichauf et al. | | |
| 2006/0076081 A1 | 4/2006 | Gleichauf et al. | | |
| 2007/0084862 A1 | 4/2007 | Jakab et al. | | |
| 2012/0189508 A1 | 7/2012 | Kreidler | | |
| 2015/0053703 A1 | 2/2015 | Kreidler et al. | | |

FOREIGN PATENT DOCUMENTS

| | | |
|---|---|---|
| DE | 102004020805 B3 | 1/2006 |
| DE | 102008053301 A1 | 4/2010 |
| DE | 202011001772 U1 | 4/2011 |
| DE | 202013007581 U1 | 9/2013 |
| EP | 2179746 A1 | 4/2010 |
| WO | 03041604 A1 | 5/2003 |

OTHER PUBLICATIONS

German Search Report for German Application No. 10 2017 117 624.1, dated Apr. 10, 2018 with translation, 11 pages.
Office Action received in German Appln. 10 2017 117 624.1 dated Jun. 8, 2020, 11 pages. (with translation).

* cited by examiner

US 11,490,982 B2

MODULARLY STRUCTURED LID FOR A STERILE CONTAINER AND FILTER COVERING FOR SUCH A LID

CROSS REFERENCE TO RELATED APPLICATIONS

This application is the United States entry of International Application No. PCT/EP2018/070732, filed Jul. 31, 2018, which claims the benefit of priority of German Application No. 10 2017 117 624.1, filed Aug. 3, 2017. The contents of International Application No. PCT/EP2018/070732 and Gelman Application No. 10 2017 117 624.1 are incorporated by reference herein in their entireties.

FIELD

The invention relates to a modularly structured lid for a sterile container, to a sterile container having such lid and to a filter covering for such lid.

BACKGROUND

Sterile containers are basically known from prior art and have been in use in medicine especially for sterilizing surgical instruments, implants and the like and for temporarily storing and, resp., transporting the same after sterilization. Objects to be sterilized in general are initially inserted into the sterile container or, resp., into a trough-shaped first container part of the sterile container. Subsequently, a lid-shaped second container part or a lid is disposed at or, resp., on the trough-shaped first container part and the two container parts are closed relative to each other. The closed sterile container is supplied to a sterilizer. Therein the objects to be sterilized provided in the interior of the container are sterilized in any sterilization process (e.g. hot air sterilization, steam sterilization etc.).

It is known from prior art to equip sterile containers with filter units/filters which are intended to prevent germs, bacteria or the like from penetrating the sterile container and to enable sterile fluid exchange during sterilization. The filter units frequently can be mounted and dismounted from an inner side of the sterile container/from inside and are disposed at an inner side of the lid on a gas exchange portion of the lid which is especially perforated. At an outer side of the lid, the gas exchange portion is covered by an external cover/filter covering which serves for protecting the filter device against mechanical influences, for example during transport or storage.

In the sterile container lids known from prior art, the filter coverings are basically mounted ex works already on lid components of the sterile container lid. Said known integral solutions for a sterile container lid frequently are difficult to handle for a user, especially as the filter covering cannot be easily removed from the lid component and a user cannot inspect/view the filter from outside. Filter units mounted from inside therefore are inspected for possible damage only after the sterilized objects have been removed by a sterile user. If it is found that the filter unit is damaged or is not present at all, the removed objects must be sterilized again, a possibly contaminated instrument bench on which the removed objects have been placed in the meantime, must be cleaned and the sterile user must change clothes, where necessary.

SUMMARY

Against this background, it is the object of the present invention to avoid or at least alleviate the afore-mentioned drawbacks from prior art. In particular, a sterile container and, resp., a sterile container lid shall be provided which a user can handle more easily and which facilitates inspection of a filter unit/filter without previous opening of the sterile container.

To begin with, the invention relates to a modularly structured lid for a sterile container or, resp., of a sterile container comprising: a lid component which has at least one gas exchange portion, which is in particular perforated, on which on the inner side of the lid at least one filter device can be/is arranged, and at least one filter covering which is preferably (at least partially) transparent and which (completely) covers the at least one gas exchange portion on an outside of the lid and, resp., by means of which the at least one gas exchange portion can be (completely) covered, wherein the lid component has at least one, especially standardized, clip receiving portion and the filter covering has at least one, especially standardized, clip portion (or vice versa) by means of which the filter covering and the cover component can be interlocked to each other, in particular by clipping, and can be mounted and removed without tools.

A central aspect of the present invention is the modular structure of the lid. In accordance with the invention, the lid component and the filter covering constitute two separate components which can be made available to a user both in a mounted condition and in a dismounted/separate condition. The lid component preferably is a component that is adapted to completely cover and close a trough-shaped container part of a sterile container. The filter covering/external covering serves for protecting the filter device, which may be, for example, a filter, filter element, combination of filter holder and filter element etc., against mechanical influences (e.g. pointed/sharp-edged objects which may pierce or cut the filter) and prevents/reduces penetration of liquids into the sterile container. The filter device preferably can be arranged at an inner side of the lid/of the sterile container on a gas exchange portion of the lid component and completely covers said gas exchange portion which, further preferred, has a plurality of perforations/holes so that gas exchange between an inner side of the sterile container/lid and an outer side of the sterile container/lid can (exclusively) take place via the filter device. When the filter covering is mounted on the lid component, the gas exchange portion is preferably completely (over its entire surface) covered by the filter covering.

Further preferred, the lid component has at least one, preferably two, standardized receiver(s)/at least one, preferably two, standardized clip receiving portion(s) which is/are suited to positively receive therein filter coverings having different characteristics, each of which includes at least one, preferably two, standardized engaging portion(s)/at least one, preferably two, standardized clip portion(s). For example, different filter coverings that differ as to material or cost, as to their mechanical properties, leak properties and as to their preferred intended use (e.g. different sterilization processes) can be made available to a user. The various filter coverings optionally can be exchanged, according to the invention, so that a filter covering adapted in its properties to the respective field of application can be used.

The fact that the filter covering and the lid component can be (positively) interlocked to each other and can be mounted and removed without tools/without the use of tools allows to achieve easy handling and any retrofitting by further developed filter coverings. Moreover, after completed sterilization the filter covering can be easily removed manually from the lid component and a condition of the filter device can be inspected by a user without the user having to open the sterile container. For example, the user can see whether the filter device is inserted and is possibly damaged, or if a process indicator is attached to the filter device, can check whether the filter device has been subjected to a process similar to sterilization. Of preference, the filter covering is therefore removed after each sterilizing operation and is re-mounted, which is also accompanied by improved cleaning of both the lid component and the filter covering.

The filter covering may preferably be made in one piece (at least partially) from transparent plastic material, preferably by injection molding. This offers the further advantage that a user can view the filter device even when the filter covering is mounted on the lid component. In addition, the filter covering is thus realized at low cost as well as for simple handling and manufacture.

Basically, a generic lid component of a sterile container (such as of the present sterile container according to the invention) has, as already described before, a substantially flat/planar upper side/outside of the lid (hereinafter also referred to as lid component main plane) which is surrounded by a frame usually/optionally preferably (adhesively) formed thereon by beading/deep-drawing, which frame can be dimensioned so that, when the lid component is attached to the trough-shaped container part, the frame encompasses the outer side of the edge of the through-shaped container part. Moreover, the gas exchange portion forming at the outside of the lid defines a plane which is raised/offset in height against the lid component main plane. The lid component main plane as well as the plane defined/spanned by the gas exchange portion are interconnected via a base/transition portion surrounding the gas exchange portion in frame shape, said base/transition portion being preferably formed integrally on the lid component main plane.

According to a preferred development of the invention, at the preferably standardized clip receiving portion of the lid component a recess or a shell-type handle recess/indentation (with respect to the lid component main plane) is provided at which the lid component, especially via recess/indentation side surfaces or flanks formed thereon, merges from the lid component main plane into a recess base area (possibly extending in parallel to the lid component main plane) which is offset against the lid component main plane by a first height downward (toward an inner side of the lid/of the sterile container) and via the transition portion being undercut/withdrawn or S-shaped at least in this area merges from the recess base area into the gas exchange portion which is offset against the lid component main plane (possibly equally in parallel), especially by a second height upward (toward an outer side of the lid/outer side of the sterile container) against the lid component main plane.

In other words, preferably at each of opposing sides of the gas exchange portion a shell-type handle or indentation is formed on the lid component main plane, the indentation edge of which facing the gas exchange portion forms a respective undercut (S-shaped cross-section) in which the preferably equally opposing clip portions of the filter covering (resiliently) interlock, when said undercut is placed on the gas exchange portion and, resp., the transition portion/base (such as in the form of a generally known keep-fresh pack with a lid). If the filter covering is to be removed again, in the area of the shell-type handles/indentations merely the lower edge area of the filter covering (facing the lid component main plane) has to be seized by the finger tips and the filter covering has to be removed elastically over the respective undercut.

Of preference, the (standardized) clip portion of the filter covering is in the form of a C-shaped/clamp-shaped side portion/end portion/strip of the filter covering and at the C-shaped side portion a laterally outwardly projecting grip portion is arranged which is manually operable when mounting and dismounting the filter covering on the lid component due to the shell-type handle/indentation formed in this area, as already described in the foregoing.

The clip portion is preferably formed at a side/end/edge portion of the filter covering as a portion bent away in clamp shape/C shape from an upper side of the filter covering (hereinafter also referred to as filter covering main plane). In other words, the filter covering is laterally delimited at least in portions by the clip portion on at least one side/edge/end. The grip portion extends preferably in parallel to the filter covering main plane outward away from the clip portion.

When the filter covering is mounted on the lid component, it is of advantage when the clamp-shaped side portion/end portion of the filter covering which forms the clip portion engages in or is clipped in the undercut transition portion of the clip receiving portion of the lid component, as equally already indicated in the foregoing.

Clipping the filter covering onto/into the lid component provides, especially when the clip portion and the grip portion of the filter covering are disposed/provided on a side/edge/end of the filter covering, a suitable mechanical connection by which the filter covering and the lid component can be interlocked with each other and can be mounted and removed without tools.

In other words, the clip portion is preferred to be a clamp-shaped side portion/end portion of the filter covering and the clip receiving portion is preferred to have an undercut portion, wherein when the filter covering is mounted on the lid component the clamp-shaped side portion of the filter covering engages in/is clipped into the undercut portion of the clip receiving portion.

One advantageous example embodiment provides for the filter covering to include two clip portions which are disposed on opposite, preferably parallel, sides and/or ends of the filter covering and for the lid component to include two clip receiving portions which are disposed on opposite, preferably parallel, sides and/or ends of the gas exchange portion and, when the filter covering is mounted on the lid component, for the two clip portions to engage in/be clipped into the two clip receiving portions.

When mounting the filter covering on the lid component, preferably at first the first clip portion is inserted into the first clip receiving portion. Subsequently, the second clip portion is pressed into the second clip receiving portion by manually operating the grip portion while the filter covering is reversibly elastically bent open. When the filter covering is dismounted from the lid component, the filter covering is pressed downwards at a central portion thereof and is pulled at one of the two grip portions, thus causing the filter covering to be reversibly elastically bent open and to be removed from the lid component.

Especially preferred, the filter covering is made from amorphous thermoplastic and is transparent and enables the filter device to be visually inspected from the outside of the lid without previous dismounting of the filter covering from the lid component.

When the filter covering is transparent, a condition thereof can be inspected by a user without the filter covering having to be dismounted from the lid component. For example, the user can see whether the filter device is inserted, is possibly damaged, or can check, if a process indicator has been applied to the filter device, whether the filter device has been subjected to a process similar to sterilization. When the filter covering is further made from amorphous thermoplastic, on the one hand the elasticity of the filter covering required for mounting and dismounting is provided along with sufficient stiffness and strength (for fastening the filter covering to the lid component), on the other hand the entire filter covering is enabled to be manufactured at low cost in one piece by injection molding.

Moreover, the invention relates to a sterile container having a trough-shaped container portion and a lid as afore-described.

In addition, the invention relates to a filter covering for a sterile container lid, especially for a lid as afore-described, for completely covering at least one gas exchange portion, which is especially perforated and is provided on a lid component of the sterile container lid, at an outside of the lid which is integrally made from, preferably transparent, plastic material and includes at least one, especially standardized, clip portion, preferably two standardized clip portions, which is/are adapted to be interlocked, especially by clipping, to an, especially standardized, clip receiving portion provided on the lid component and by means of which the filter covering can be mounted and dismounted on the lid component without using tools.

Of preference, the clip portion is in the form of a C-shaped/clamp-shaped side portion/end portion of the filter covering and, on the C-shaped side portion, a laterally outwardly projecting grip portion is arranged which is manually operable for mounting and dismounting the filter covering on the lid component.

Further, the filter covering preferably includes two clip portions which are disposed on opposite, preferably parallel sides and/or ends of the filter covering and are adapted to positively engage in two clip receiving portions disposed on opposite, preferably parallel, sides and/or ends of the gas exchange portion, when the filter covering is mounted on the lid component.

Advantageously, the filter covering is further made from amorphous thermoplastic and is transparent and enables a filter device which can be arranged on an inner side of the lid of the gas exchange portion to be visually inspected from an outer side of the lid without previous dismounting of the filter covering from the lid component.

BRIEF DESCRIPTION OF THE DRAWING FIGURES

Hereinafter, the invention shall be illustrated in detail by way of figures, wherein.

The figures are merely schematic and serve exclusively for the comprehension of the invention. Like elements are provided with like reference numerals.

DETAILED DESCRIPTION

Figure 1:
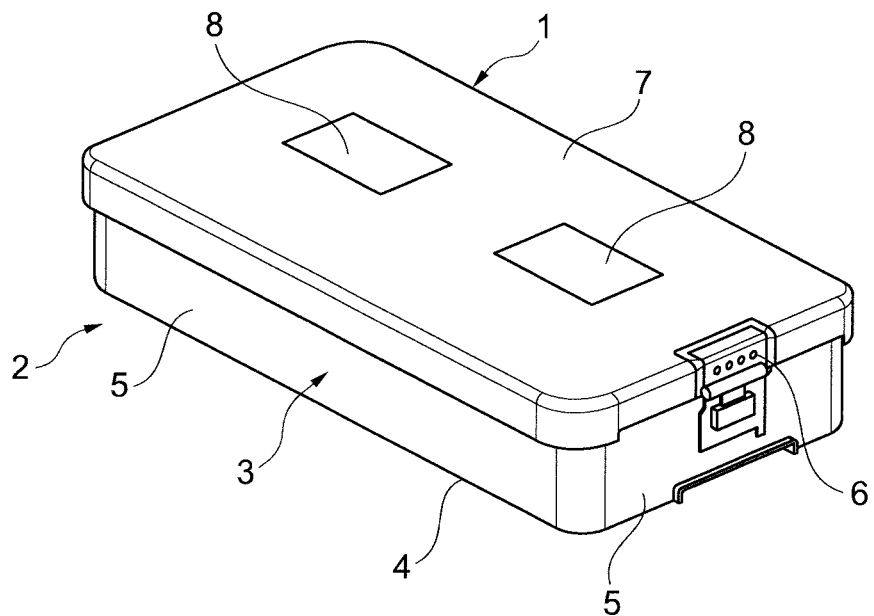
FIG. 1 shows a perspective view of a sterile container having a lid and a receiving container.

FIG. 1 illustrates a perspective view of a lid 1 according to the invention for a sterile container 2 which closes a trough-shaped receiving container 3. The receiving container 3 comprises a container bottom 4 and container walls 5 rising from said container bottom. The receiving container 3 and the lid 1 are closed by means of a closure 6. The lid 1 includes a lid component 7 covered on the outside by two filter coverings 8. According to the invention, also one filter covering 8 (one gas exchange portion on the lid component 7) or more than two filter coverings 8 (more than two gas exchange portions on the lid component 7) may be provided. Beneath the filter coverings 8, portions that are perforated or are in the form of a perforated plate (not shown) are provided on the lid component 7 in FIG. 1. The lid component 7 completely covers the receiving container 3. The lid component 7 and the filter covering 8 are separate components.

Figure 2:
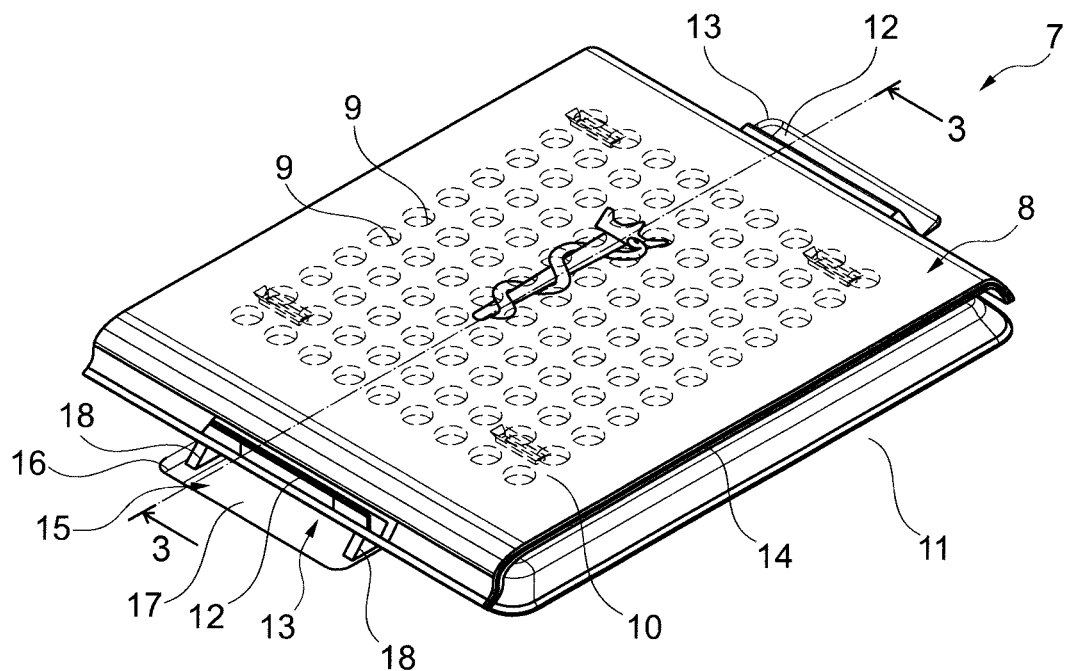
FIG. 2 shows an enlarged perspective view of a filter covering arranged on a lid component.

FIG. 2 illustrates an enlarged perspective view of a filter covering 8 arranged on the lid component 7. The filter covering 8 shown in FIG. 2 is transparent/translucent and is made, for example, from amorphous plastic/thermoplastic by injection molding. Due to the transparency of the filter covering 8, perforations/holes 9 provided on a gas exchange portion 10 of the lid component 7 are visible. The perforations/holes 9 of the gas exchange portion 10 permit fluid exchange during sterilization. It is already evident from FIG. 2 that the gas exchange portion 10 is a portion protruding from a lid component main plane 11. The filter covering 8 is rectangular and plate-shaped or disk-shaped (in the form of a thin plate/disk). In particular, a height/thickness of the filter covering 10 is negligible in relation to its length and width.

At each of two opposing, preferably shorter, sides (of the rectangle) the filter covering 8 has a clip portion 12 which is provided on a central portion of the respective side (of the rectangle). Each of the clip portions 12 of the filter covering 8 is positively received in clip receiving portions 13 of the lid component 7. On the (rectangular) sides of the filter covering 8 including the clip portions 12, the filter covering is bent and in portions abuts on the projecting gas exchange portion 10 of the lid component and at the end side abuts on the lid component main plane 11. At the two further, equally opposing and preferably longer sides (of the rectangle) the filter covering 8 is arranged to be spaced apart from the gas exchange portion 10, especially by about 2 mm. During sterilization, fluid exchange may take place especially via the narrow gap 14 provided between the filter covering 8 and the gas exchange portion 10.

Each clip receiving portion 13 has, inter alia, a recess 15 which is composed of recess side surfaces 16 and a recess base area 17. Projections 18 of the filter covering 8 are guided at two opposing recess side surfaces 16. In other words, the projections 18 of the filter covering 8 are arranged adjacent to the two opposing recess side surfaces 16, when the filter covering 8 is mounted on the lid component 7.

Figure 3:
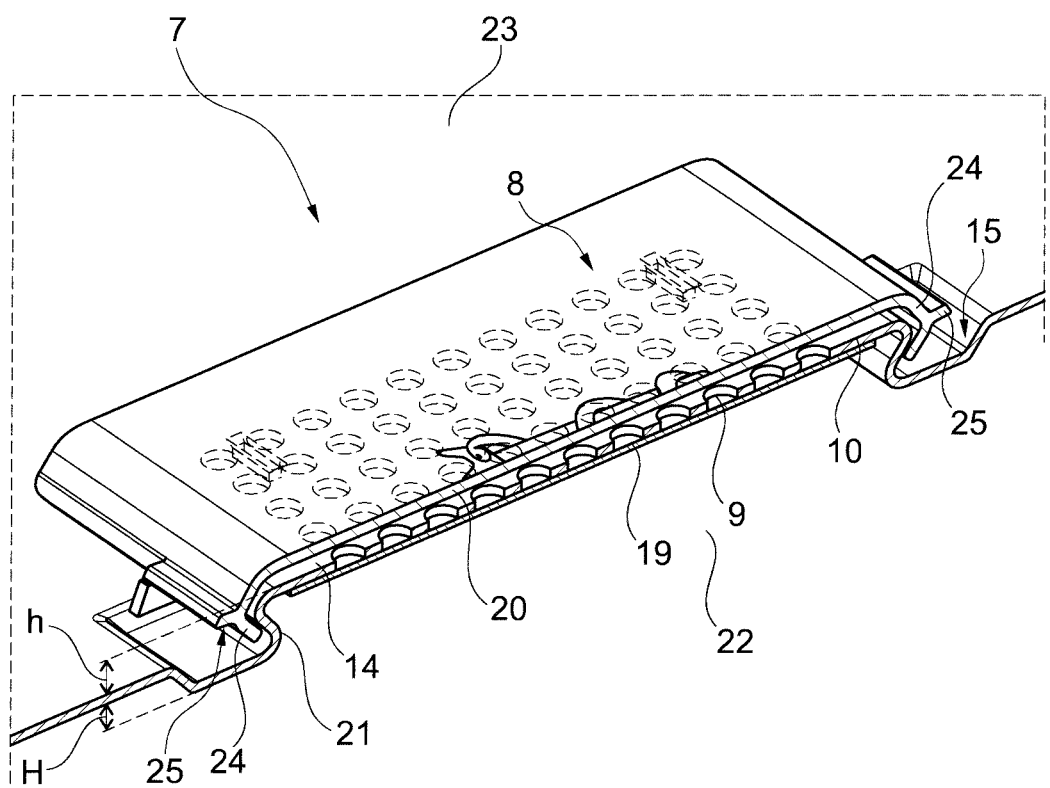
FIG. 3 shows a perspective view cut along the axis 3-3 in FIG. 2 of the filter covering arranged on the lid component.

FIG. 3 illustrates a perspective view cut along the axis 3-3 in FIG. 2 of the filter covering 8 disposed on the lid component 7. Here it is first of all evident that, on a lower side/toward an inner side of the lid/an inner side of the sterile container of the gas exchange portion 10 having the holes/perforations 9, a filter 19 which is a rectangular thin filter element and completely covers all holes/perforations 9 of the gas exchange portion is arranged. Further, is becomes more apparent from FIG. 3 that the filter covering 8 and the gas exchange portion 10 are spaced apart from each other or, in other words, a gap 14 is defined between the gas exchange portion 10 and a filter covering main plane 20.

It is further apparent from FIG. 3 that, adjacent to the recess side faces 16 and the recess base area 17, the recess 15 has an S-shaped transition portion 21. In other words, at the recess 15 the lid component 7 merges, via recess side surfaces 16, from the lid component main plane 11 into the recess base area 17 and merges, via the S-shaped transition portion 21, from the recess base area 17 into the gas exchange portion 10. The recess base area 17 is offset against the lid component main plane 11 by a height H downwards/toward an inner side of the lid 22. The gas exchange portion 10 is offset against the lid component main plane 11 by a height h upwards/toward an outside of the lid 23. The recess base area 17, the lid component main plane 11 and the gas exchange portion 10 are parallel to one another. The S-shaped transition portion 21 extends in S shape between the recess base area 17 and the gas exchange portion 10.

Moreover, it is evident from FIG. 3 in which way the clip portions 12 of the filter covering 8 are configured. The clip portions 12 are clamp-shaped/C-shaped end portions/(rectangular) side portions 24 which extend at two opposite (rectangular) sides of the filter covering downwards/toward an inner side of the lid 22 from the filter covering main plane 20 in clamp shape/C shape. A grip portion 25 extends to protrude laterally outwards from the clamp-shaped/C-shaped (rectangular) side portions 24. The grip portion 25 is in parallel to the filter covering main plane 20.

When the filter covering 8 is mounted on the lid component 7, the clamp-shaped/C-shaped (rectangular) side portions 24 of the filter covering 8 are clipped onto the S-shaped transition portions 21 of the lid component 7 or, resp., the C-shaped (rectangular) side portions 24 cling to the S-shaped transition portions 21 so that the filter covering 8 and the lid component 7 are thus interlocked with each other. Clipping of the clip portions 12 of the filter covering 8 onto/into the clip receiving portions 13 of the lid component 7 is facilitated especially by the elasticity of the employed amorphous thermoplastic.

The invention claimed is:

1. A modularly structured lid for a sterile container comprising:
    a lid component which has at least one gas exchange portion which is perforated and on which at least one filter device can be arranged, and
    at least one filter covering by which the at least one gas exchange portion can be covered on an outside of the lid, wherein
    the lid component has at least one clip receiving portion and the filter covering has at least one clip portion by which the filter covering can be interlocked to the lid component, and can be mounted and dismounted without tools,
    wherein at the clip receiving portion of the lid component a trough-shaped recess is provided at which the lid component merges from a lid component main plane into a recess base area and merges, via an S-shaped transition portion, from the recess base area into the gas exchange portion.

2. The modularly structured lid according to claim 1, wherein the clip portion of the filter covering is configured as a clamp-shaped side portion of the filter covering and on the clamp-shaped side portion there is arranged a laterally outwardly projecting grip portion which is manually operable when the filter covering is mounted and dismounted on the lid component.

3. The modularly structured lid according to claim 2, wherein when the filter covering is mounted on the lid component, the clamp-shaped side portion of the filter covering positively engages in the S-shaped transition portion of the lid component.

4. The modularly structured lid according to claim 1, wherein the clip portion is a clamp-shaped side portion of the filter covering and the clip receiving portion includes a S-shaped portion, wherein when the filter covering is mounted on the lid component the clamp-shaped side portion of the filter covering engages in the S-shaped portion of the clip receiving portion.

5. The modularly structured lid according to claim 1, wherein the filter covering has two clip portions which are arranged on opposite sides and/or ends of the filter covering, and the lid component has two clip receiving portions which are arranged on opposite sides and/or ends of the gas exchange portion, and when the filter covering is mounted on the lid component, the two clip portions engage in the two clip receiving portions.

6. The modularly structured lid according to claim 1, wherein the filter covering is made from amorphous thermoplastic and is transparent for visually inspecting the filter device from the outside of the lid without previous dismounting of the filter covering from the lid component.

7. A sterile container comprising:
    a trough-shaped container part; and
    the modularly structured lid according to claim 1.

* * * * *